(12) United States Patent
Amirkhanian et al.

(10) Patent No.: US 8,163,152 B1
(45) Date of Patent: Apr. 24, 2012

(54) METHOD AND APPARATUS FOR HIGH SPEED CARBOHYDRATE ANALYSIS

(75) Inventors: Varouj Amirkhanian, La Crescenta, CA (US); Ming-Sun Liu, Brea, CA (US); Andras Guttman, San Diego, CA (US)

(73) Assignee: Qiagen Sciences, LLC, Germantown, MD (US)

( * ) Notice: Subject to any disclaimer, the term of this patent is extended or adjusted under 35 U.S.C. 154(b) by 682 days.

(21) Appl. No.: 11/983,814

(22) Filed: Nov. 9, 2007

Related U.S. Application Data

(60) Provisional application No. 60/858,049, filed on Nov. 9, 2006.

(51) Int. Cl.
G01N 27/447 (2006.01)
G01N 27/453 (2006.01)

(52) U.S. Cl. .......................... 204/455; 204/605
(58) Field of Classification Search .......... 204/450–455, 204/601–605
See application file for complete search history.

(56) References Cited

U.S. PATENT DOCUMENTS

| | | | |
|---|---|---|---|
| 5,213,669 A | | 5/1993 | Guttman |
| 5,964,999 A | * | 10/1999 | Guttman et al. ............. 204/455 |
| 6,770,698 B1 | * | 8/2004 | Chu et al. ..................... 524/458 |
| 6,828,567 B2 | * | 12/2004 | Amirkhanian et al. .... 250/458.1 |
| 7,198,701 B2 | * | 4/2007 | Ueda et al. ................... 204/451 |
| 7,208,072 B2 | | 4/2007 | Amirkhanian et al. |
| 7,309,409 B2 | | 12/2007 | Amirkhanian et al. |
| 2005/0016852 A1 | | 1/2005 | Amirkhanian et al. |
| 2005/0189219 A1 | | 9/2005 | Amirkhanian et al. |

OTHER PUBLICATIONS

Guttman et al. "Capillary electrophoriesis separation of oligosaccharides: I. Effect of operational variables," Electrophoreis 1994, 15, 1518-1522.*
Guttman et al. "Capillary gel electrophoresis separation of high-mannose type oligosaccharides derivatized by 1-aminopyrene-3,6,8-trisulfonic acid," Electrophoresis 1995, 1906-1911.*
Wikipedia entry for polyethylene glycol downloaded Aug. 15, 2011.*

* cited by examiner

Primary Examiner — Alex Noguerola
(74) Attorney, Agent, or Firm — Liu & Liu

(57) ABSTRACT

A cost-effective multi-channel capillary gel-electrophoresis system for highly efficient, high speed, high throughput, carbohydrate analysis. In one aspect of the present invention, a high-performance capillary electrophoresis analyzer system has been optimized for carbohydrate analysis application. The system uses a multiplexed/time-staggered fluorescence type detection mechanism, with an integrated fiber optic array-based technology and a novel disposable gel-cartridge. Twelve carbohydrate samples are automatically injected, electrophoretically separated, detected and analyzed simultaneously by using a multiple usage and disposable multi-capillary gel-cartridge. Using commercially available labeling agent such as APTS (representing 8-Aminopyrene-1,3,6-trisulfonic acid, trisodium salt) as an indicator, the capillary electrophoresis-based carbohydrate system/analyzer provides high resolving power in 2-15 minutes of separations. The system can hold a total of 96 samples, which can be automatically analyzed within 30-60 minutes. This affordable fiber optic based fluorescence detection system can be used in laboratories for high speed carbohydrate sequencing & screening applications.

20 Claims, 11 Drawing Sheets

METHOD AND APPARATUS FOR HIGH SPEED CARBOHYDRATE ANALYSIS

This application claims the priority of U.S. Provisional Patent Application No. 60/858,049, filed on Nov. 9, 2006. This Provisional Patent Application is fully incorporated by reference herein, as if fully set forth herein. All other applications, patents, documents and references identified in the disclosure herein below, are fully incorporated by reference as if fully set forth herein.

BACKGROUND OF THE INVENTION

1. Field of the Invention

The present invention relates to bio-analysis system and method, and particularly an improved system and method for carbohydrate analysis.

2. Description of Related Art

During the last two decades, chromatographic separation of complex carbohydrate mixtures has undergone a remarkable development. The earlier strategies involved the use of gas chromatography (GC) and GC/MS (Mass Spectroscopy) for quantification of monosaccharides and linkage determinations. To increase the volatility and hydrophobicity of sugar molecules, permethylation was utilized in the gas-phase analyses. While permethylation is still practiced to this date to enhance certain analytical objectives, low volatility of larger oligosaccharides made the GC approach somewhat unattractive. A search for optimum separation media in the liquid-phase separation of glycans has been evident for a number of years. Additionally, carbohydrates in their native state yield poor detection in chromatography, because of the lack of chromophores in their molecules. A derivatization (typically occurring at the reducing end of oligosaccharide chains) can introduce a chromophore or a fluorophore for the sake of detection and simultaneously enhance the solutes hydrophobicity for an appropriate separation.

A significant breakthrough in carbohydrate chromatographic analysis was achieved through combining anion-exchange chromatography of glycans with pulsed-amperometric detection (PAD). Under highly alkaline pH conditions, carbohydrates become charged, interactive with the ion-exchange resins, and detectable electrochemically. Following a series of incremental improvements, this form of chromatography was commercialized, becoming a standard tool of glycobiology. While this combination allows fairly effective separations of unmodified carbohydrates and quantification in the picomole range, further structural investigations of the separated glycans are complicated by their recovery from high-salt media. Carbohydrate analysis applied in laboratories also utilizes slab gel-based electrophoresis technologies. However, slab gel electrophoresis for carbohydrate analysis is labor-intensive, low throughput and low resolution. Traditional gel-based electrophoresis methods currently used for carbohydrate analysis take hours, if not days, to produce results with many cumbersome manual procedures, which are subject to human errors.

High-performance capillary electrophoresis (HPCE) now represents a set of powerful electromigration techniques whose impact has been felt in virtually all areas of biochemical analysis, including carbohydrate separations. HPCE is a micro fluidic approach to gel electrophoresis, whose greatest advantage is its diverse range of applications. CE technology is commonly accepted by the biotechnology industry, as a reliable, high resolution and highly sensitive detection tool.

While the first applications of HPCE to sugar analysis were described more than a decade ago, high interest HPCE methodologies remain to this date. Unprecedented separations of highly complex oligosaccharide mixtures were demonstrated, as was the resolution of sugar optical isomers and extremely sensitive detection of fluorescently labeled glycans from single biological cells through laser-induced fluorescence (LIF) detection. To comply with the sensitivity requirements, labeling with fluorophoric group is often the requirement for HPCE carbohydrate applications. CE with laser-induced fluorescence (LIF) is one of the most powerful analytical tools for rapid, high sensitivity and high-resolution bio-analysis type applications.

CE with laser-induced fluorescence (LIF) combined with derivatization agents, such as APTS, have been sought for detection of glycans. APTS was utilized for the labeling of N-glycans released from ribonuclease B and fetuin prior to their analysis by gel CE. It was also utilized in the analysis of N-glycans by others, including glycoproteins such as ribonuclease B, fetuin, recombinant human erythropoietin, karrikrein, and chimeric recombinant monoclonal antibody.

Recently, a complete method for analysis of N-glycans has been derived from glycoproteins. It is based on a combination of specific chemical and enzymatic conversions coupled with CE/LIF. N-Glycans are released enzymatically from glycoproteins and derivatized with APTS under mild reductive amination conditions to preserve sialic acid and fucose residues. The method successfully profiled the heavily sialylated N-glycans. A method for multistructure sequencing of N-glycans by gel CE and exoglycosidase digestions has also been devised.

The current CE systems with laser-induced fluorescence (LIF) detection mechanism that use multiple capillaries/channels for high-throughput applications are complicated in design and operation of the instrument. These systems utilize scanning optical detection mechanisms, which are much more bulky, sensitive in optical alignment and naturally more expensive than the traditional slab gel based systems. The expensive multi-capillary electrophoresis-based systems are thus out of reach for all but a few well-funded laboratories and seem to be a barrier for the expansion of the high-throughput carbohydrate analysis business.

It is therefore desirable to develop a simpler and much improved technology to provide lower per sample-cost, rapid and multi-channel type analysis with high efficiency, sensitivity, throughput, and ultimately, standardization for routine carbohydrate analysis.

SUMMARY OF THE INVENTION

The present invention provides a cost-effective multi-channel capillary gel-electrophoresis system for highly efficient, high speed, high throughput, carbohydrate analysis (e.g., carbohydrate sequencing and screening). This system can be used in laboratories to replace traditional gas chromatography, and slab gel and single channel capillary electrophoresis devices for high-speed and low cost applications of carbohydrate. In one aspect of the present invention, a high-performance capillary electrophoresis analyzer system has been optimized for carbohydrate analysis applications.

In one embodiment, the system uses a multiplexed/time-staggered fluorescence type detection mechanism, with an integrated fiber optic array-based technology and a novel disposable gel-cartridge. Twelve carbohydrate samples are automatically injected, electrophoretically separated, detected and analyzed simultaneously by using a multiple usage and disposable multi-capillary gel-cartridge. Using commercially available labeling agent such as APTS (representing 8-Aminopyrene-1,3,6-trisulfonic acid, trisodium salt) as an indicator, the capillary electrophoresis-based carbohydrate system/analyzer provides high resolving power in 2-15 minutes of separations. The system can hold a total of 96 samples, which can be automatically analyzed within 30-60 minutes. This affordable fiber optic based fluorescence detection system can be used in laboratories for high speed carbohydrate sequencing & screening applications.

The multi-channel CE carbohydrate analysis system in accordance with the present invention improves the speed of separation and resolution of carbohydrate molecules. Benefits of the system over slab gel electrophoresis include time savings (reducing separation time from 3 to 4 hr with slab gel methods to 10 min with the inventive system); labor and consumable reduction (reducing the possibility of human error by eliminating manual intervention, while reducing testing material such as gel, buffer, dye, and markers by 50%); increased sensitivity, resolution and biohazardous waste reduction.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF ILLUSTRATED EMBODIMENTS

Figure 1:
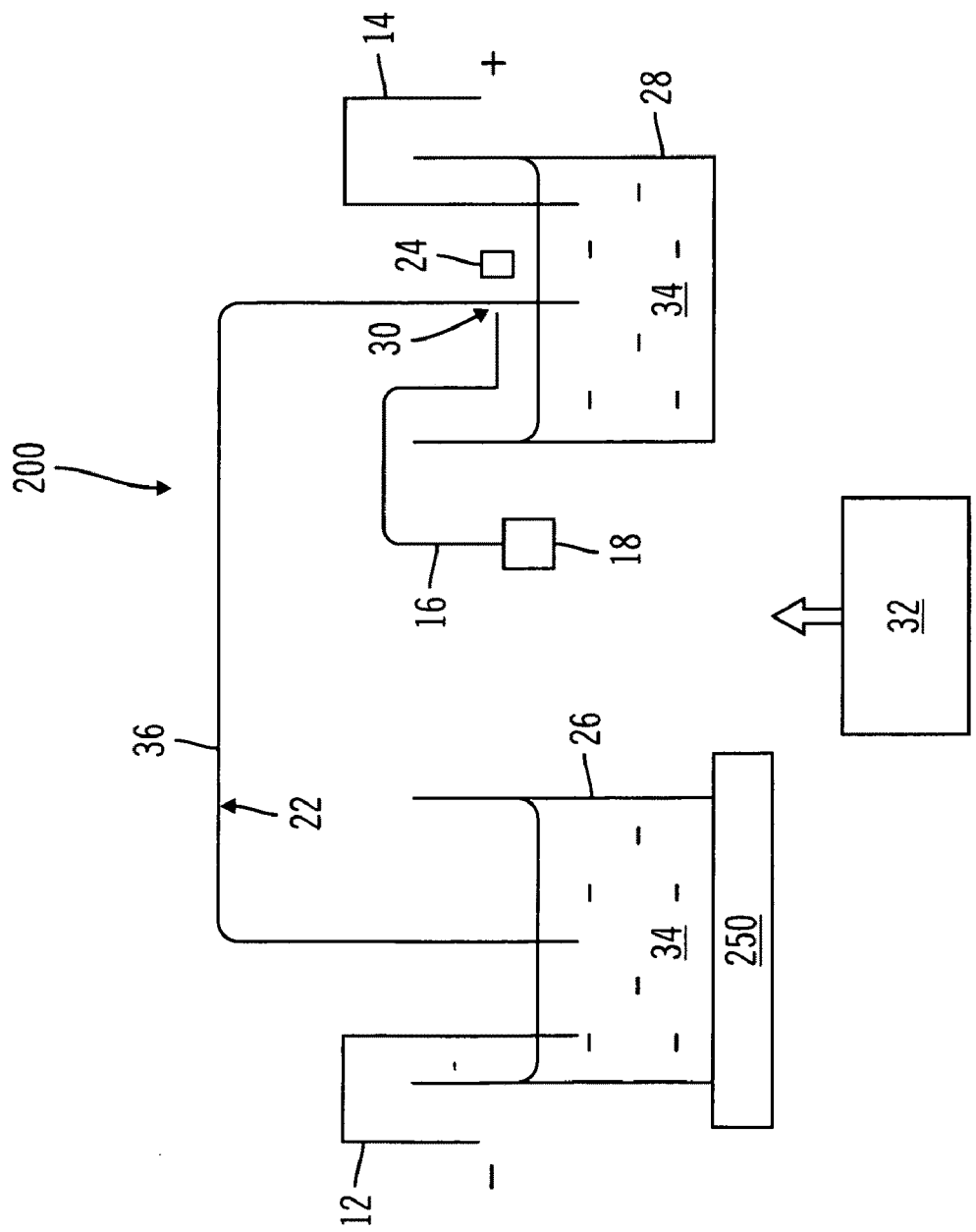
FIG. 1 is a schematic representation view of a capillary electrophoresis system in accordance with one embodiment of the present invention.

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides a cost-effective multi-channel capillary gel-electrophoresis system for highly efficient, high-speed, high throughput, carbohydrate analysis (e.g., carbohydrate sequencing and screening). This system can be used in laboratories to replace traditional gas chromatography devices, and slab gel and single channel capillary electrophoresis devices for high-speed and low cost applications for carbohydrates. In one aspect of the present invention, a high-performance capillary electrophoresis analyzer system has been optimized for carbohydrate analysis application. In the illustrated embodiment, a low-cost and high-throughput, 12-channel fluorescence-based capillary electrophoresis instrument equipped with a disposable gel-cartridge is developed for rapid carbohydrate separation and detection.

Capillary Electrophoresis

Capillary electrophoresis (CE) generally is a micro fluidic approach to electrophoresis (micro-channel device to simplify gel electrophoresis). Its greatest advantage is its diverse range of applications. CE technology is commonly accepted by the biotechnology industry specifically in the nucleic acid-based testing as a reliable, high resolution and highly sensitive detection tool.

CE with laser-induced fluorescence (LIF) is also one of the most powerful analytical tools for rapid, high-sensitivity and high-resolution carbohydrate analysis/testing. However, due to the complexity of the equipment that detects and measures carbohydrate samples and the difficulty in preparing the samples, the existing carbohydrate analysis procedures are often time-consuming and expensive. However, CE-LIF-based multiple-channel systems with complicated scanning optical detection mechanisms are much more expensive than traditional gas chromatography and single channel CE based carbohydrate analysis systems. These expensive CE-LIF-based systems are thus out of reach for all but a few well-funded laboratories and seem to be a barrier for the expansion of the carbohydrate analysis applications.

It is therefore desirable to reduce the size, number of parts, and cost of equipment, to ease sample handling during the process, and in general, to have a simplified, low cost, high sensitivity detector, which would allow for simpler technologies/products that are sensitive, specific, high-throughput, cost-effective and rapid. Such tools will ultimately provide standardization for routine carbohydrate analysis.

BioCal Technology, Inc. (which is wholly owned by eGene, Inc.), the assignee of the present invention, developed a CE-based automated instrument (e.g., Model HDA-GT12 Analyzer System). The illustrated embodiment of the automated instrument is based on BioCal's CE instrument, which incorporates low-cost and sensitive optical detection technology, integrated reagents cartridge and micro-fluidic electrophoresis principle for a real-time fluorescent analysis, to form a sensitive and accurate bioagent detection (carbohydrate analysis) system. The system is designed to be high-throughput, easy-to-use, portable, inexpensive, very robust and for field operation/applications. The cartridge developed by BioCal (e.g., Model GCK-CARB specifically for carbohydrate analysis) is designed to be supported by the instrument, with all essential cartridge elements aligned and coupled to support elements in the instrument. The cartridge is held with respect to sample trays that can be moved in relation to the capillary separation channels in the cartridge.

Overview of CE System

FIG. 1 is a schematic representation of a capillary electrophoresis (CE) system 200 in accordance with one embodiment of the present invention (e.g., Model CarbCE Analyzer). The CE system 200 generally comprises a capillary separation column 22 (e.g., 200-500 µm O.D.), which defines a separation channel 36 (e.g., 5-200 µm I.D.). The capillary column 22 may be made of fused silica, glass, polyimide, or other plastic/ceramic/glassy materials. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may be a running buffer, or in the illustrated embodiment a sieving gel buffer specifically formulated for carbohydrate analysis under the prescribed operating conditions). For purpose of carbohydrate analysis, a low pH linear polymer gel with no intercalating dye is used in accordance with one embodiment of the present invention.

One end of the capillary column 22 is submerged in a reservoir 28 of running buffer/gel 34. The other end of the capillary column 22 is coupled to the sample vial 26. It is understood that other detection configurations implemented in a system similar to the CE system 200. A radiation detector 24 is positioned outside a transparent section of the capillary walls at detection zone 30. An excitation fiber 16 extends from a radiation source 18 (e.g., LED or laser) and is directed at the detection zone 30 outside the walls of the column. Electrodes 12 and 14, that are part of the cartridge assembly are coupled to the buffer reservoirs 26 and gel reservoir 28 to complete the electrophoresis path.

Overview of CE Separation and Analysis

In operation, a prepared biological sample (e.g., a carbohyrate sample) in the sample vial 26 with a tagged fluorophore (i.e APTS) is introduced into the far end of the capillary column 22 away from the detection zone 30 by any of a number of ways (e.g., electrokinetic injection from the sample reservoir).

When a DC potential (e.g., 1-30 KV) is applied between electrodes 12 and 14, the sample components migrate under the applied electric potential along the separation channel 36 (e.g. carbohydrate molecules that are negatively charged travels through the sieving gel toward a positive electrode as shown in FIG. 1) and separate into bands of sample components (carbohydrate fragments). The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For the automated system, a controller 32 (discussed below in connection with FIG. 5) on the electronic board 64 (FIG. 4) controls the operations of the CE system 200.

Capillary Cartridge

In accordance with one aspect of the present invention, the capillary column for electrophoresis may be a part of a removable cartridge that can be separated from the system for storage, transport or reuse. Different cartridges may be pre-assembled with different content, for example, a different gel-chemistry, with the content of the cartridge identified. Visual indicators may be provided to identify the cartridge and its contents. For example, a label (e.g., with a bar-code) or separate information sheet may be applied to the cartridge. In addition, in view of the reusability of the cartridge and defined usage or shelf life of the contents of the cartridge, a separate log may be associated with the particular cartridge for keeping track of the usage of the cartridge. A reusable capillary cartridge for use with a CE instrument could include a mechanism to automatically track information associated with a particular cartridge. The cartridge tracking data key feature is more fully described in copending patent application Ser. No. 11/022,313, which is fully incorporated by reference herein.

Figure 2:
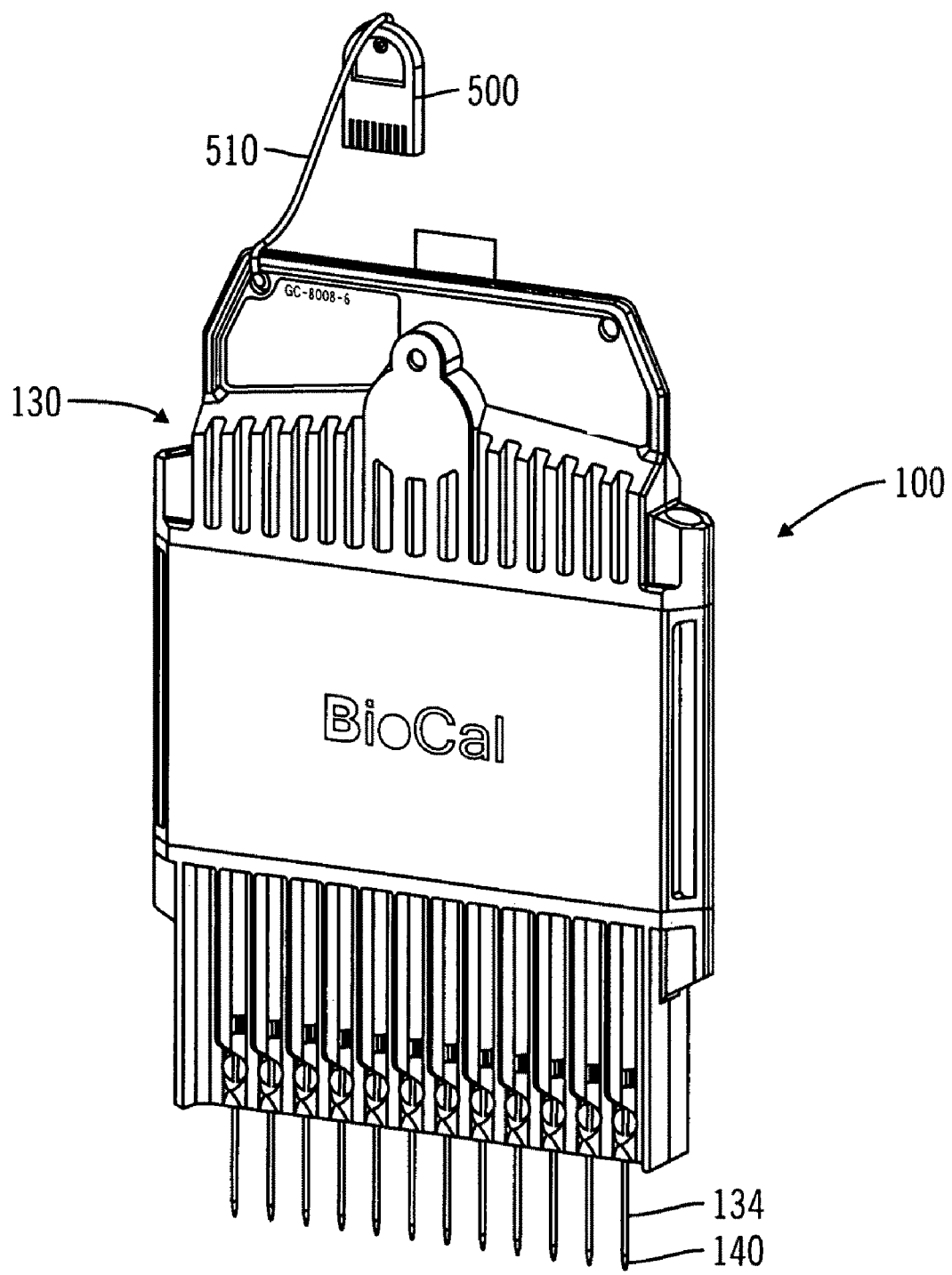
FIG. 2 is a perspective view of a capillary cartridge having a tracking device in accordance with one embodiment of the present invention.

FIG. 2 is a perspective view of the CE cartridge having a tracking data key in accordance with one embodiment of the present invention. The multi-channel capillary cartridge 200 includes twelve detection zones (schematically represented as 30 in FIG. 1), defined by capillaries 140 held in a cartridge body. A data key 500 is associated with the cartridge 100 (e.g., by a tether or cord 510 as shown). Details relating to the data key 500 is disclosed in copending application Ser. No. 11/022,313. The cartridge 100 includes a twelve-channel fused silica capillary array that is used for separation and detection of the samples as part of a disposable and/or portable, interchangeable cartridge assembly 100. The cartridge 100 shown in FIG. 2 holds up to 12 capillaries 140, 12-18 cm long. The cartridge 100 is integrated with a top, outlet buffer reservoir 130 common to all capillaries 140, which, when the cartridge 100 is installed in the CE system shown in FIGS. 3 and 4 (discussed below) is directly coupled by the interface mechanism 300 to a modular compressed gas source 78, such as a replaceable pressurized gas cartridge of an inert, compatible or non-reactive gas (e.g., Nitrogen, compressed air, $CO_2$, etc.) or a pressure pump. Appropriate pressure plumbing, including tubing, pressure valve and solenoid controls, is provided. (Details of such plumbing are omitted, since it is well within one skilled in the art to configure such plumbing given the disclosure herein of the functions, features and operations of the system 200.) The pressure source 78 provides the required gas pressure to fill-up all the 12-capillaries with the sieving gel contained in the reservoir 130 and to purge the gel from the previous run from the capillaries during the refilling process. Depending on the viscosity of the gel, pressures of up to 40 PSI may be applied to the capillaries 140 through the gel-filled reservoir 130.

Figure 6:
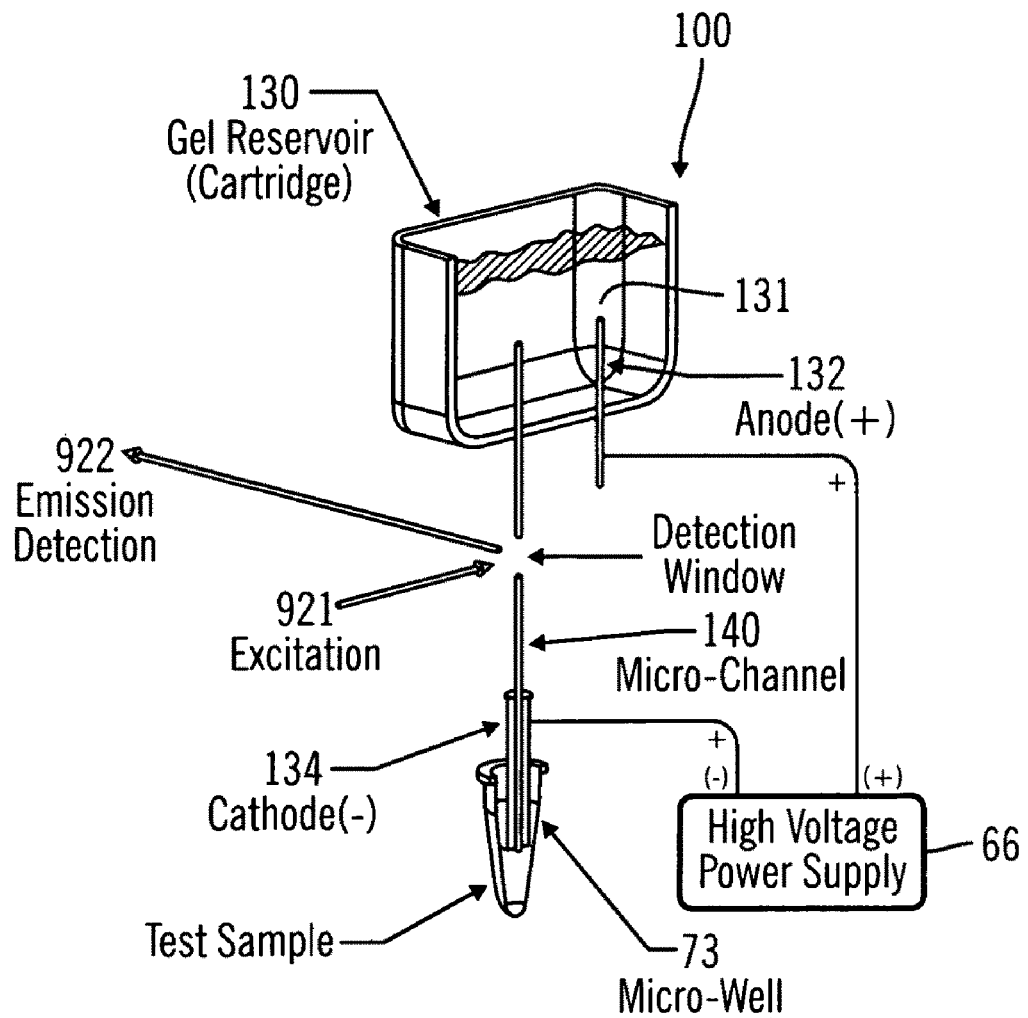
FIG. 6 is a schematic view of the capillary cartridge in relation to detection system and applied power in accordance with one embodiment of the present invention.

Referring to FIG. 6, the gel-cartridge 100 includes an integrated reservoir 130 containing a separation support medium (e.g., a gel matrix buffer) 131, which is common to all capillaries 140. The chemistry of the medium 131 and the characteristics of the capillaries 140 (e.g., capillary size, coating and length) are defined for each cartridge 100. The disposable gel-cartridges 100 can be packaged with small bore I.D. capillaries (i.e. 10-50 µm ID, 12-30 cm long) combined with low current (i.e., at low resistivity) and low viscosity type formulated linear polymer gel-matrix to provide high speed (shorter separation time) and higher resolution separations of carbohydrate fragments. The smaller bore capillaries (12-capillary cartridge) combined with the special formulated separation buffer/gel-matrix can achieve 250 or more continuous runs with a total current of <120 (typically 10-20 µA) without any damage to the gel matrix or loss of overall separation resolution.

The cartridge gel-reservoir 130 is equipped with a built in common electrode anode 132 (equivalent to anode 14 in FIG. 1) for all 12-capillaries 140, and each depending end of the capillaries 140 is provided with an external coaxial cathode 134. The anode 132 and cathodes 134 are automatically connected by the interface mechanism 300 to the high voltage power supply 76 (FIG. 4) for electrophoresis when installed inside the system 200. A fan or Peltier cooler (not shown) on the adjacent structure to the cartridge 100 may be provided to provide temperature control of the cartridge. In addition or in the alternate, the cartridge may have vent holes (input and output) for air circulation (temperature controlled air to be introduced to the cartridge from the instrument side). Depending on the heat generated during CE separation, the cartridge may simply be exposed to ambient temperature, with no auxiliary cooling features.

Figure 3:
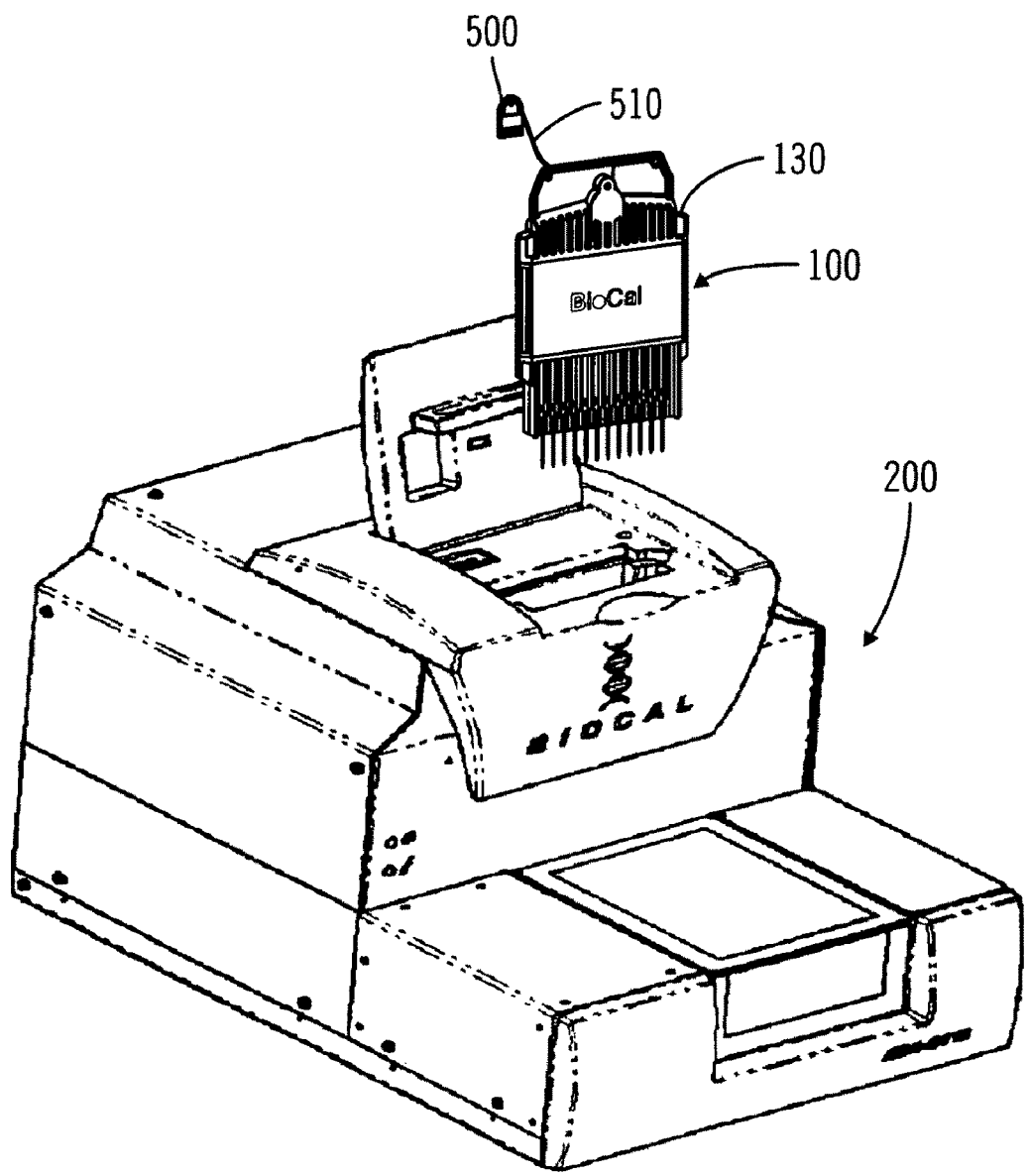
FIG. 3 is a perspective external view of a bio-analysis instrument that uses the capillary cartridge of FIG. 2, in accordance with one embodiment of the present invention.
Figure 4:
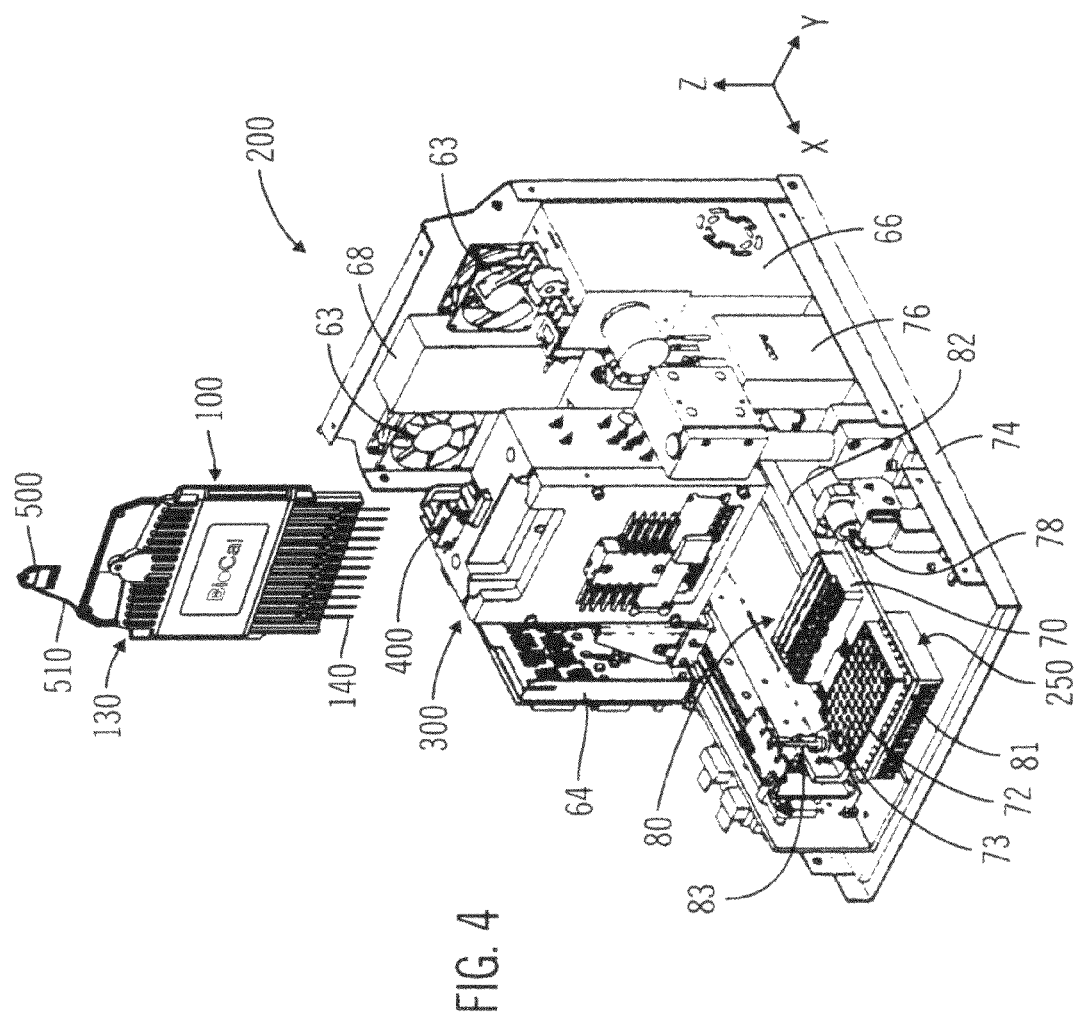
FIG. 4 is a perspective internal view of the bio-analysis instrument of FIG. 3, in accordance with one embodiment of the present invention.

In one embodiment, the cartridge 100 is received in the automated CE system 200 shown in FIGS. 3 and 4. A power supply 66 (FIG. 4) provides DC power to the CE system 200 to be supplied to the cartridge, as will be further explained below.

Further details of the cartridge may be referenced to the copending application Ser. No. 10/059,993, which is fully incorporated by reference herein.

Multiple Capillary Cartridge Based CE System

FIG. 4 shows an overall perspective view of the internal components of the CE system 200 (e.g., a carbohydrate analyzer). FIG. 3 is an external view of the system. The CE system 200 incorporates an interface mechanism 300, in accordance with one embodiment of the present invention. The interface mechanism 300 supports a multi-channel cartridge 100 in accordance with the one embodiment of the present invention, which provides easy handling of multi-channel separation columns, and allows easy optical coupling of the detection zones to the detection optics of the CE system 200.

The fully automated carbohydrate analysis system 200 has a base 74, supporting a modular X-Z mechanism 80 having a sample tray support frame 81. The X-Z mechanism 80 supports and moves a buffer plate 70 in relation to the multi-capillary cartridge 100 supported by the interface mechanism 300, and a sample holder (e.g., a 96-well micro-titer plate 72) which may be held in an optional sample preparation device 250. Specifically, the mechanism 80 comprises an X mechanism 82 for moving the support frame 81 along the X-direction relative to the cartridge 100, and a Z mechanism 83 for moving the cartridge in the Z direction relative to the support frame 81. The sample preparation device 250, if provided, may be controlled by a thermoelectric controller 68 (see FIG. 5).

Figure 7:
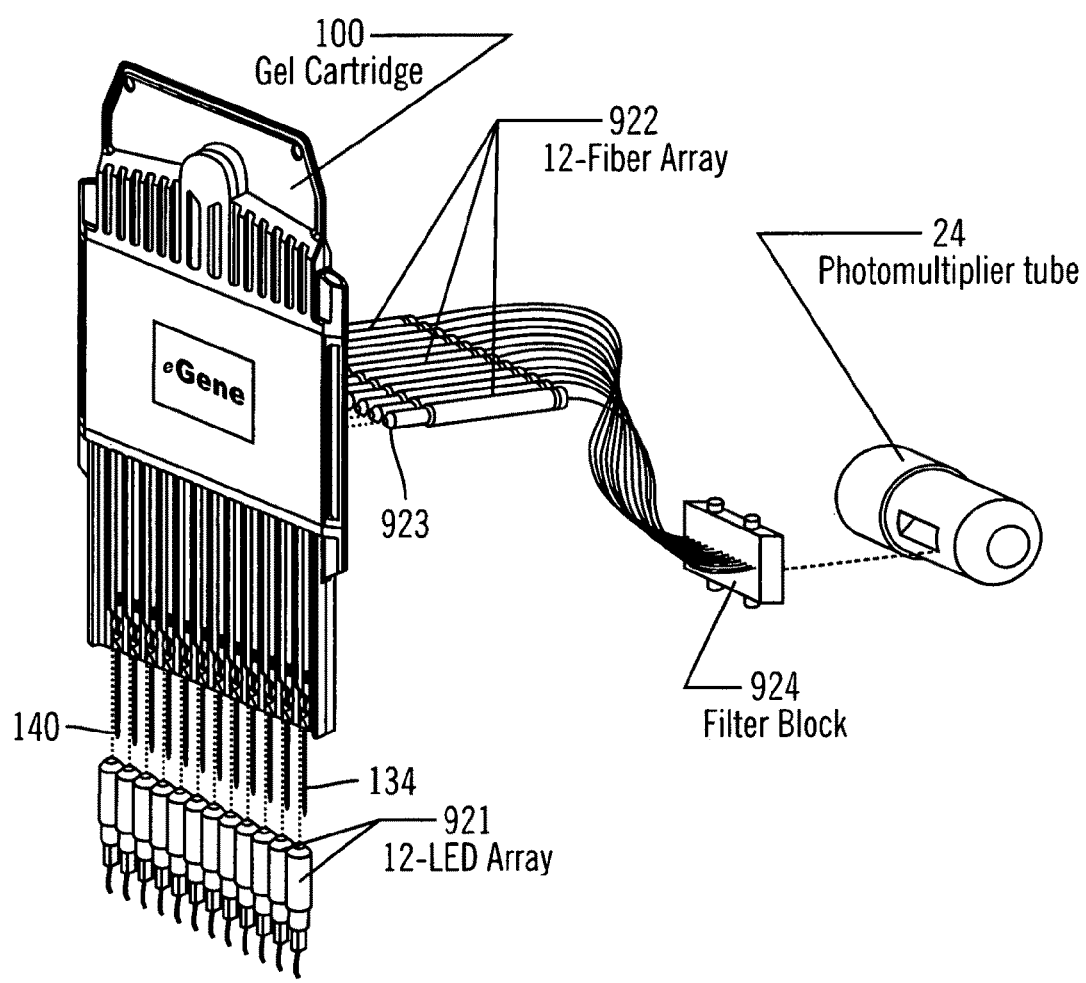
FIG. 7 is a partial perspective view of the capillary cartridge in relation to detection system in accordance with one embodiment of the present invention.

Referring also to FIGS. 6 and 7, twelve excitation LEDs 921 are time-multiplexed (with a sampling frequency of 10-100 Hz), producing multiplexed signals to the 12 separation micro-channels (capillary tubes 140) and proportionally twelve time-staggered emitted fluorescence signals (FIG. 7) are then collected by 12-micro-ball lenses 923 and are coupled to twelve emission detection optical fibers (12-fiber array) 922, which are relayed down to a single photomultiplier tube (PMT detector) 24 via a filter block 924. The gel-cartridge 100 supports 12 fused silica capillaries 140 for CE separation (FIGS. 6 and 7).

Other structures and operations of the interface mechanism 300 of the CE system 200 may be referenced to the copending U.S. patent application Ser. No. 10/823,382, which is fully incorporated by reference herein. The cartridge interface accomplishes quick and reliable interface connections to the disposable gel contained capillary cartridge 100. These interface connections include a gas pressurization connection (not shown in FIG. 7), high voltage connections (anode 132 and cathodes 134), and precision optical connections. The interface also provides precise and repeatable mechanical positioning of the cartridge, to accurately position the components of the cartridge in relation to the support elements in the CE system 200, including positioning the capillary tips in relation to external sample or buffer reservoirs, found on 96-well titer plate, for example. Additionally, given the interface provides separate electrical, optical and pneumatic connections to each separation channel, there would be channel-to-channel isolation from cross talk both electrically and optically and insulation to the rest of the instrument from high voltage.

Detection System

U.S. Pat. No. 6,828,567 is fully incorporated by reference herein, which more specifically discloses the time staggered/multiplexed detection scheme that can be adopted in the CE system 200.

Control of the Automated System 200

The CE system 200 provides an integrated controller to operate the various components of the system. The operations of the CE system 200, including the interface mechanism 300 with the I/O port 400, detection system, power supply, X-Y control system, etc., are controlled by a controller 32 interfacing with an external user control interface (e.g., a PC 918), to coordinate the functions described herein.

Figure 5:
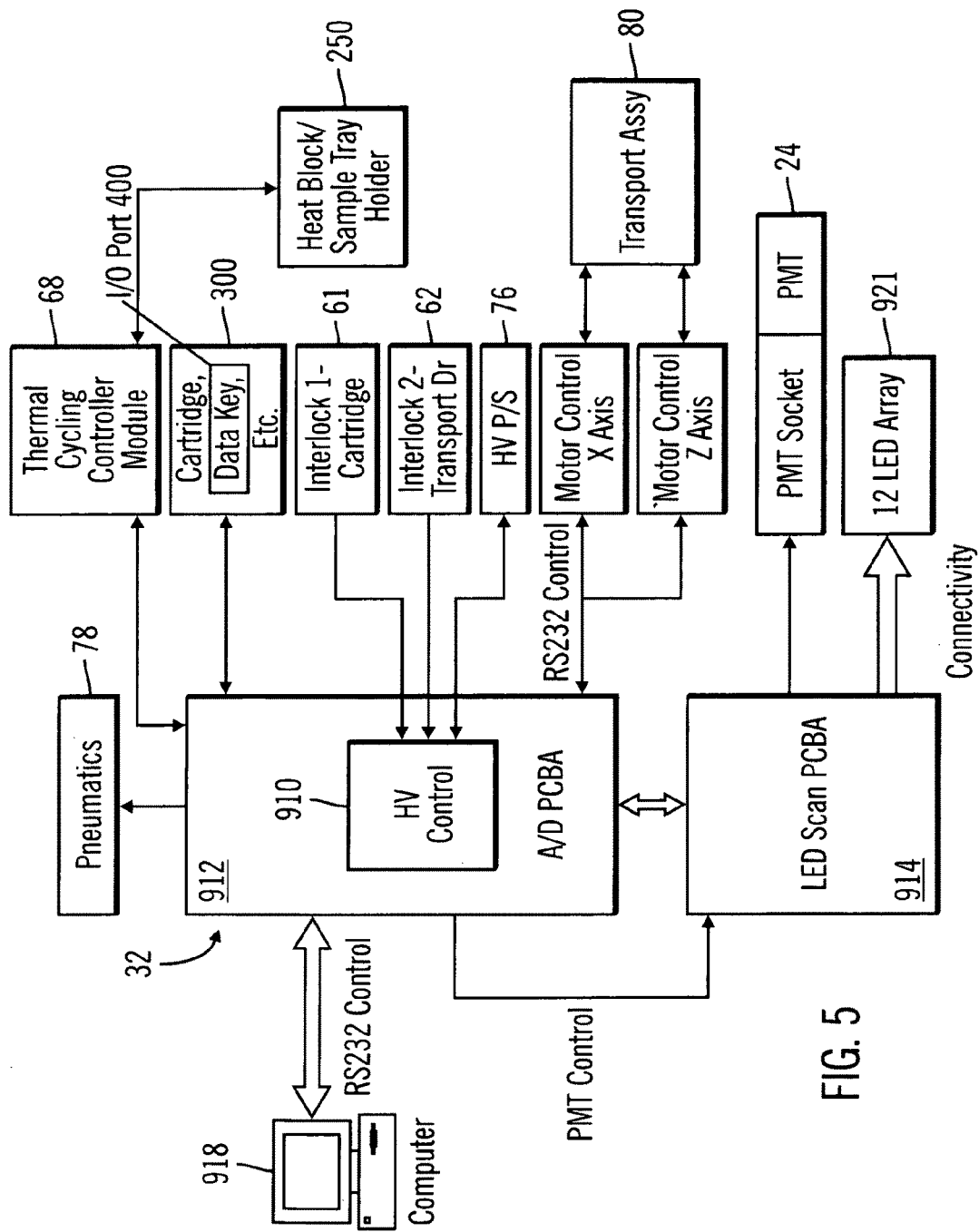
FIG. 5 is a block diagram of the control system for the bio-analysis instrument in accordance with one embodiment of the present invention.

Referring also to FIG. 5, in accordance with one embodiment of the present invention, the block diagram of the controller 32 for the CE system 200 is illustrated. The controller 32 comprises a processor as part of the A/D Board (LED Processor PCBA) 912 with CPU 910 for converting detection signals received from the detector 24 (e.g., a PMT) to corresponding digital signals, coming from LEDScan PCBA interface 914 for transferring and receiving signals to and from respective parts of the CE system 200 by instructions from the CPU 910. The A/D (LED Processor PCBA) interface 912 is coupled to the various actuators and the I/O port 400 in the interface mechanism 300 to control and connect (using the interface mechanism 300) at least high voltage power supply 76, pneumatics 78 (hidden from view in the interface mechanism 300 in FIG. 2), motor controls (X-Z sample/buffer tray) 80 and interlocks (cartridge and transport doors) 61 and 62 (details of these are not shown in the interface mechanism 300 in FIG. 2). The A/D or LED Processor PCBA 912 also controls the high-voltage power supply 76 for sample injection and electrophoresis functions of the CE system 200, a circuit 914 (LEDScan Board) for modulating the excitation radiation source (e.g., LEDs) 921 and the detector module 24 of the CE system 200. Details of the modulation of the excitation radiation source may be referenced to copending U.S. patent application Ser. No. 10/060,052, which had been fully incorporated by reference herein.

The A/D (LED Processor PCBA) 912 may be further coupled to an external personal computer 918, which in turn performs data processing or additional control function for the CE system 200, e.g., using BioCal's BioCalculator Software to control various features and functions of the automated multi-channel CE system 200.

The components of the controller 32, with the exception of the PC 918, may be packaged as an electronic board 64 (FIG. 4) and cooling fans 63, on board the CE system 200 and electrically coupled to the PC 918 via a serial port (not shown), or they may be part of a separate controller module outside of the CE system 200. The CPU 910 and/or the PC 918 are programmed to accomplish the various control functions and features for the CE system 200. In one embodiment, the PC 918 can be configured to provide the user control interface for the CE system 200 (e.g., user initiation of the connection sequence of the interface mechanism 300). It would be within a person skilled in the art to implement the program code given the functions and features disclosed herein. In an alternate embodiment, the controller 32 or components thereof may be incorporated as part of the PC 918.

Operation of CE System

Once the capillary cartridge 100 and the data key 500 have been mated to the instrument, the cartridge ID and the number of pre-programmed runs available from the cartridge 100 are read by the CE system 200 via the I/O port 400. The CE system 200 may employ an algorithm to determine if the capillary cartridge 100 has enough runs left to complete the process cycle before initiating the CE sequence. Otherwise, the CE system 200 may display an error message and the sequence is stopped. If it is determined that the capillary cartridge 100 has sufficient runs available, the CE sequence will start and number of runs is tracked by the CE system. At the end of the analysis, the number of remaining runs is calculated and sent to the data key 500 for storage.

The controller 32 of the instrument may be configured to "authenticate" the cartridge 100 and conduct an integrity check to determine if the particular cartridge 100 has the correct properties (e.g., gel-chemistry, number of channels/capillaries) for the particular sample analysis to be conducted. The instrument may also confirm that the user falls within the class of users permitted to use the particular cartridge. Further, the instrument may communicate/record information concerning usage of the cartridge 100 (e.g., usage history, sequence/method steps/parameter settings, patient I.D., test parameters, and perhaps test results). Such information provides an update to the stored information from the previous use of the cartridge. Further reading and writing can be controlled with respect to the data and information discussed above relating to the data key 500. The instrument may go through other checks to authenticate the test protocols the user wants to apply to the particular cartridge is proper, to determine if there are any limitations, restrictions or constraints, such as those noted before.

In operation of the CE analysis, the sample handling tray transport mechanism 80, with a 96-well plate (8×12) 72 and buffer tray 70, is used to introduce the carbohydrate samples (or analytes) to each capillary 140. The X-Z transport mechanism 80 indexes a row of sample carrying wells 73 in the micro-titer plate 72 under the row of capillary tips 140 and dip the tips into the well. By applying a voltage, electrokinetic injection moves a known amount of the carbohydrate sample to the beginning of the separation column 140. After injection, the carbohydrate samples from sample tray 72 may be replaced with a running buffer from tray 70. Alternatively, after injection, the transport mechanism 80 may index to move a row of 12 wells of the titer plate 72 into position under the capillaries 140 of the cartridge 100 to replace the twelve wells containing carbohydrate samples.

By applying high voltage across the total length of the capillary 140, separation of the carbohydrate sample into carbohydrate fragments is achieved. As the fragments approach the end of the capillaries 140 and enter into the detection zone, the excitation light energy (e.g., from twelve LEDs delivered by optical fibers) is directed at the detection zone, illuminating the migrating carbohydrate fragments. The detection scheme may be in a time-staggered manner as disclosed in U.S. Pat. No. 6,828,567, which has been incorporated by reference herein.

To prepare for the next run with a different sample, the old gel from the previous run is purged from the capillaries by pressuring the reservoir to refill the capillaries with fresh gel. The trays 70 carry cleaning solutions, waste collection, and samples. The purged gel is collected by one of the trays 70 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the tray 72. The above mentioned sequence of process may be programmed as one of the automated functions of the controller 32. The interface mechanism 300 provides the interfacing of support elements in the CE system 200 to the cartridge, such as high voltage, gas pressure, LED radiation source, and detection optics, as described above.

After the analysis has been completed, the cartridge 100 may be retrieved and reused when needed for another analysis at a later time or date. If a different run condition is contemplated, a different cartridge having different attributes and properties may be used instead. The data key mechanism of the present invention would automatically keep track of the usage of the different interchangeable cartridges, without requiring the user to manually keep track of such.

Common Carbohydrates

General names for carbohydrates include sugars, starches, saccharides, oligosaccharides and polysaccharides. Carbohydrates (from 'hydrates of carbon') or saccharides (Greek σάκχαρον meaning "sugar") are simple organic compounds that are aldehydes or ketones with many hydroxyl groups added, usually one on each carbon atom that is not part of the aldehyde or ketone functional group.

According to the present invention the term "carbohydrates" includes also derivatives thereof. The basic carbohydrate units are called monosaccharides, such as glucose, galactose, and fructose. The general stoichiometric formula of an unmodified monosaccharide is $(C.H_2O)_n$, or $C_n(H_2O)_n$ where n is any number of three or greater.

Further, carbohydrates according to the invention include disaccharides. Two joined monosaccharides are called disaccharides and represent the simplest polysaccharides. Common disaccharides are maltose, lactose, and sucrose.

Furthermore, carbohydrates according to the invention include oligosaccharides and polysaccharides which are composed of longer chains of monosaccharide units bound together by glycosidic bonds. Common polysaccharides are starch, glycogen, and cellulose.

For example, carbohydrates and their derivatives play major roles in the working process of the immune system, fertilization, pathogenesis, blood clotting, and development. See, also Williams, N. R., Hrsg., *Carbohydrate Chemistry*, Royal Society of Chemistry: London, (1984, 1985); Bd. 16, 17 and Ernst, B.; Hart, G. W.; Sinaÿ, P., Hrsg., *Carbohydrates in Chemistry and Biology, Part I: Chemistry of Saccharides*, Wiley-VCH: Weinheim, (2000); Bd. 1, 2 which are hereby incorporated by reference.

Carbohydrate Analysis Applications

Figure 8:
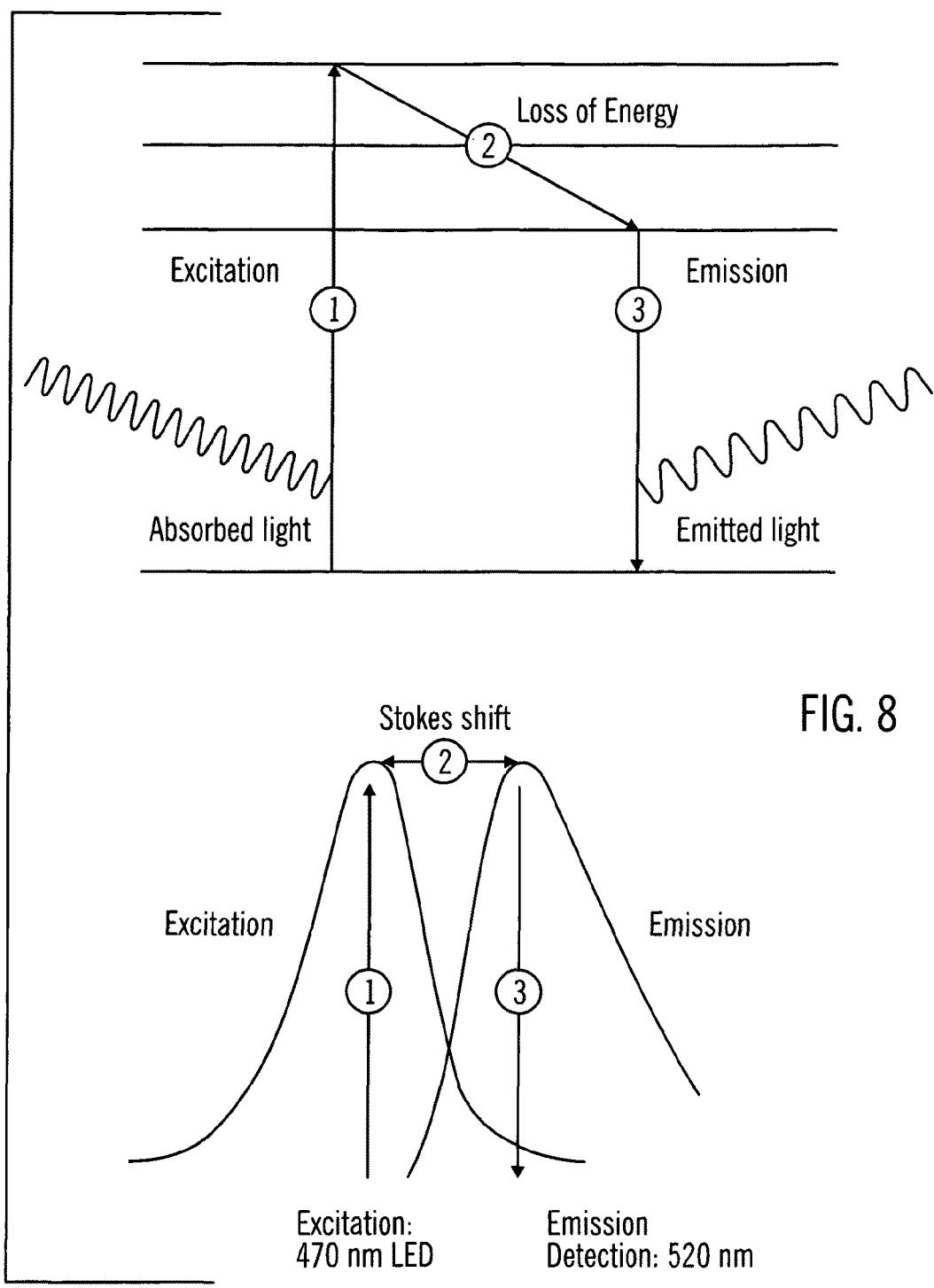
FIG. 8 illustrates the relationship between excitation and emission detection, and associate wavelengths.

The afore-described CE analysis system is optimized for high speed carbohydrate analysis (e.g., carbohydrate sequencing and screening). The HDA-GT12™ Analysis System adapted for carbohydrate analysis (e.g., a CarbCE system) provides a large-volume and low-cost carbohydrate diagnostics and analysis platform alternative to the slab gel type tools. As described above, the system implements incident radiation from a solid state laser or LED source coupled to an array of twelve optical fibers for the excitation and emission detection of separated analytes, which are directed through the boundary walls of the detection zone or the separation column (capillary tubes). In the illustrated embodiment shown in FIGS. 2-7, twelve super bright LEDs with a center wavelength of 470 nm are used for the excitation of APTS or fluorescin type dyes. The twelve excitation LEDs 921 are time-multiplexed (with sampling frequency of 10-100 Hz), twelve emission signals are then collected by 12-micro-ball lenses 923 and coupled to twelve emission detection optical fibers (12-fiber array 922), which are relayed down to a single photomultiplier tube (PMT detector 24) in a time-staggered manner. The PMT detector 24 has a specific emission filter 924 having a long pass filter at 520 nm between the collection fiber array 922 and the PMT detector 24 to be able to filter out and separate the emitted fluorescence signal of the sample from that of the LED excitation wavelengths, which are present in the optical path in the form of scattered background light produced through the capillary window, which contributes to the overall base-line noise. FIG. 8 illustrates the relationship between excitation and emission detection, and associate wavelengths.

The multi-channel gel-cartridge 100 supports multiple fused silica capillaries for the CE separation (FIGS. 2 and 7). The gel-cartridge 100 includes an integrated reservoir containing a separation support medium (e.g., a gel buffer), which is common to all capillaries (FIGS. 6 and 7). The chemistry of the medium (gel is linear polymer) and the characteristics of the capillaries (e.g., capillary size, coating and length) are defined for different cartridges. Different cartridges can be easily interchanged in the bio-separation system to suit the particular sample based separation. The short and narrow bore capillaries combined with special sieving gel provides low operating current (<200 μA) at high applied voltages (e.g., 10 KV) without the need to cool the capillaries to achieve high speed, high resolution and high performance separations/results for large volume and low cost screening of bio-molecules such as carbohydrates.

Simplifying the optical detection system design of the new instrument reduces the manufacturing cost, while improving the reliability. While the chemistry cost per test is less than half that of slab gel systems, the chemical reagent produces high resolution and detection sensitivity found in high-end capillary electrophoresis systems.

An example of sugar separations is presented below, followed with a discussion of the results in reference to FIGS. 10, 11 and 12.

Example

D-(+)-glucose, D-(+)-maltose monohydrate, maltotriose, maltopentaose, and maltoheptaose (Sigma-Aldrich, St. Louis, USA) were reconstituted in HPLC water to 1 mg/ml final concentration and 5 nmol of each solution was used in the derivatization procedure. The oligosaccharide solutions and a negative control containing 2.5 μL HPLC water (Sigma) were dried in 0.2 ml microfuge vials. The dried sugars were then labeled through reductive amination by the addition of 1 μL 0.2M 8-aminopyrene-1,3,6-trisulfonic acid (APTS) (Sigma) in 15% acetic acid and 1 μM $NaBH_3CN$ in tetrahydrofuran (Sigma) labeling reaction was incubated for 2 h at 55° C., followed by dilution with 100 μL water to stop the reaction. The final concentrations of oligosaccharide solutions were around 50 μM (49.01 μM).

The samples were diluted 500 times with HPLC water and analyzed on the eGene's CarbCE system with a multi-capillary (12) gel-cartridge (GCK-CARB). The APTS-derivatized oligosaccharides fluoresce intensely by means of the illumination of a blue light emitting diode (LED; peak wavelength: 460-470 nm) as excitation source; for the emission detection >520 nm long pass filter was used. Separations were performed in an array of 13 cm long (effective) buffer treated silica capillary columns (20 μm ID) by using an automated process programmed with a desired method (e.g., Method 0M300 disclosed below). The capillaries were filled with CARB Separation solution (Sodium acetate buffer, pH 4.5 with linear polymer). In accordance with one embodiment of the present invention, the linear polymer solution used for the gel sieving matrix comprises: [between about 0.01% and about 1.5% polyethylene oxide ("PEO"); between about 0.0% and less than about 2.0% of a second polyethylene glycol ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

In a preferred embodiment the matrix has the following components:

|      | mwt g/mol | Concentration |
|------|-----------|---------------|
| PEO  | 7000000   | 0.000607 mM   |
| PEO  | 900000    | 0.002777778 mM|
| MOPS |           | 12.5 mM       |
| Tris |           | 7.85 mM       |
| NP40 |           | 0.05%         |
| NaN3 |           | 1 mM          |
| EtBr |           | 10 mM         |

The carbohydrate gel cartridge is designed to produce high speed electrophoretic results using an automated method (e.g., the "0M300 Method") programmed in the CarbCE system for the carbohydrate sample runs, showing: an initial purge of the capillaries for 20 seconds in the wash position, carbohydrate samples injection at 3 KV for 30 seconds, electrophoresis separation at ambient temperature at 7 KV for 300 seconds with the capillary tips in the buffer position. A mixture of APTS labeled glucose, maltose, maltotriose, maltopentaose and maltoheptaose was used as a carbohydrate ladder in the separations.

The BioCalculator software provides a full automated cartridge prep, gel purging, carbohydrate sample injection and buffer separation sequence and final analyses results within about 350 seconds per row for a 12 channel type cartridge using the automated method according to the programmed sequence of steps and operation parameters discussed above.

Figure 9:
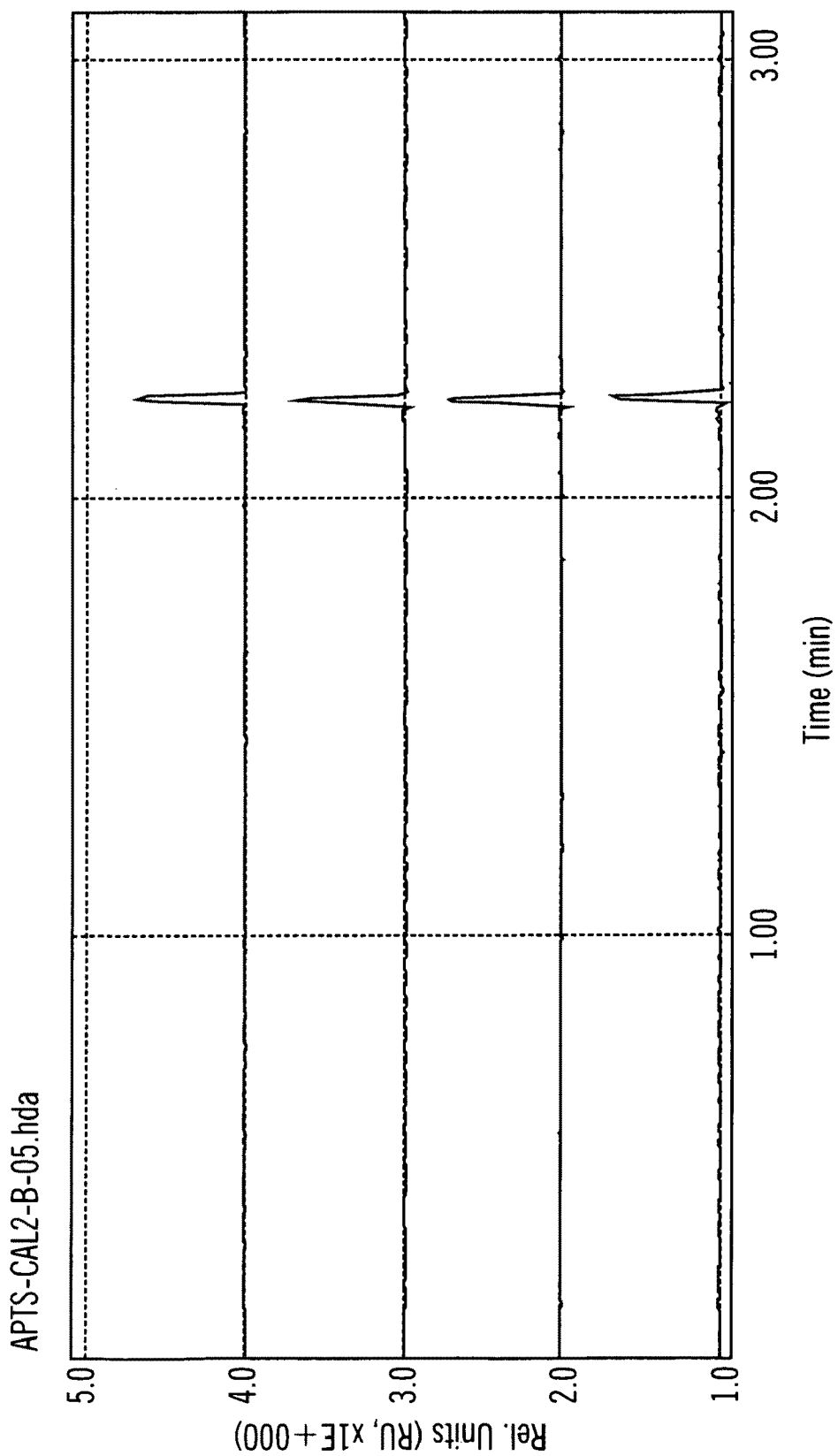
FIG. 9 shows the calibration reading of the gel cartridge.

FIG. 9 shows the calibration reading of the gel cartridge, specifically a carbohydrate 4-channel gel-cartridge, using 20 μm ID 30 cm long capillaries were calibrated with APTS (concentration: 0.1 ng/μl). In the example here, the capillary cartridge only supports 4 capillaries because the capillaries were 30 cm long and they had to be looped inside the body of the cartridge to accommodate the relative long capillaries. By using longer capillaries, separation resolution can be further improved.

Figure 10:
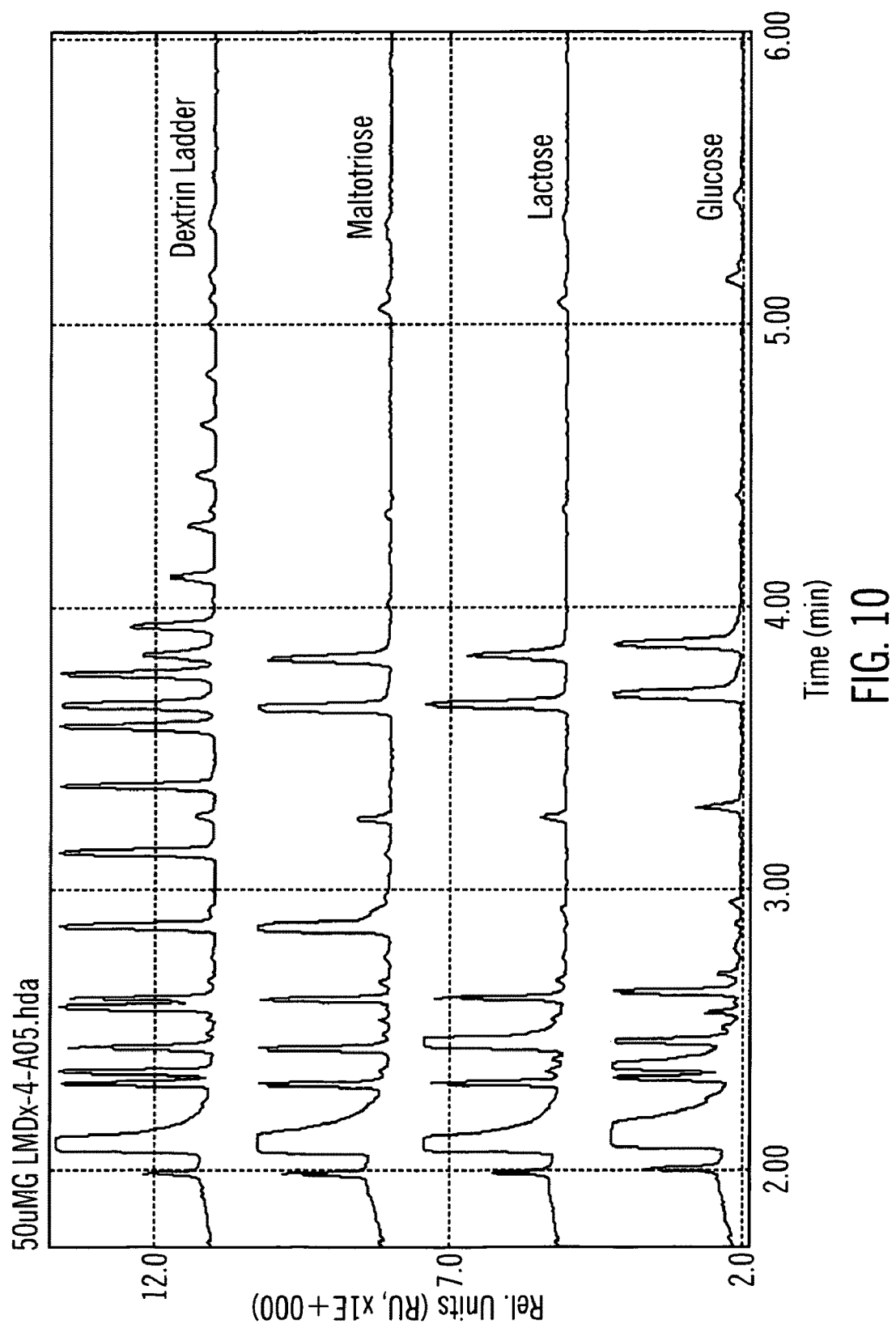
FIG. 10 is an electropherogram representing the high speed and high-resolution results of four carbohydrate type samples using the 12-capillary gel-cartridge, showing Glucose, Lactose, Maltotriose and Dextrin Ladder separations in less than 6 minutes (expanded view with 5 µM sample concentration), in accordance with one embodiment of the present invention.

FIG. 10 is an electropherogram representing the high speed and high-resolution results of four carbohydrate type samples using the capillary gel-cartridge, showing Glucose, Lactose, Maltotriose and Dextrin Ladder separations in less than 6 minutes (expanded view with 5 μM sample concentration).

Figure 11:
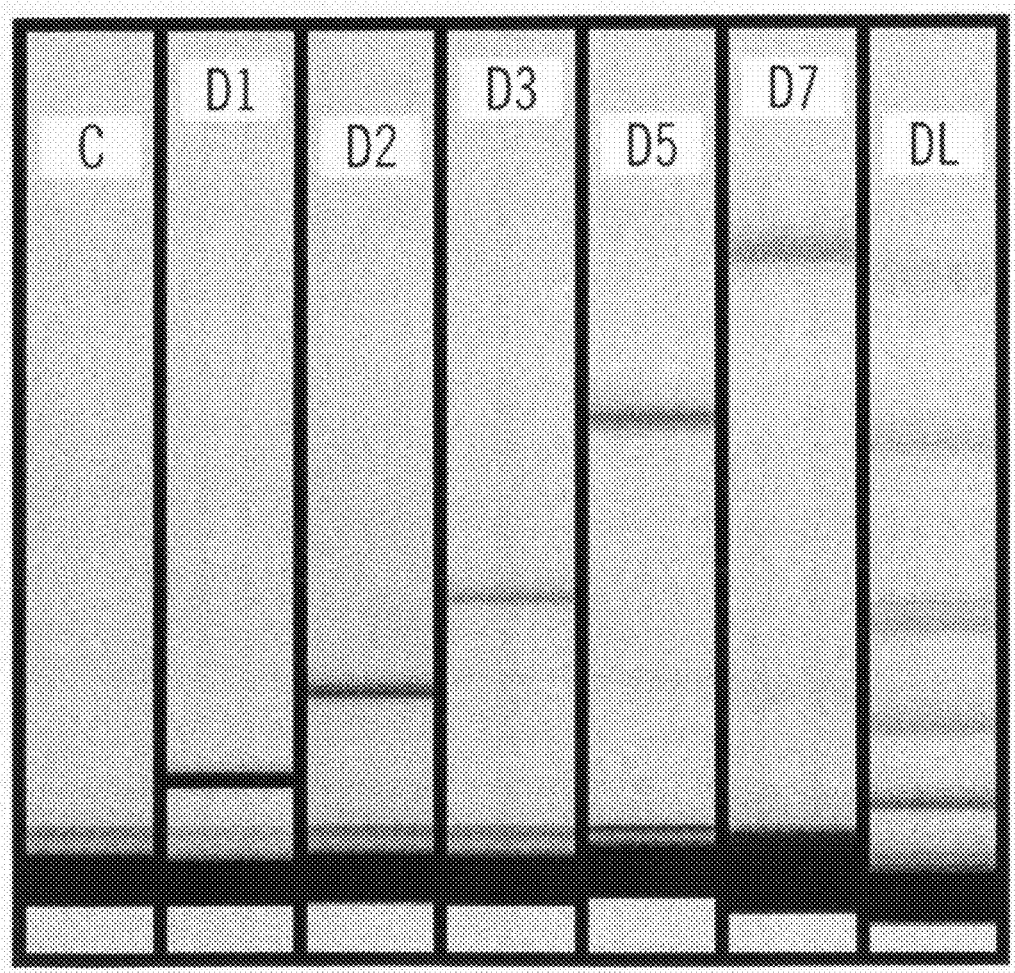
FIG. 11 shows the gel-image of 5 carbohydrate samples (sugars) analyzed by the CarbCE system, in accordance with one embodiment of the present invention.

FIG. 11 shows the gel-image of another example of 5 carbohydrate samples (sugars) analyzed by the CarbCE system with a 12-channel/capillary cartridge. The gel-image has been transformed from the detected optical detection data for each capillary channel, into an image representing tracks of separation bands which similar to separation image typically represented for gel slab separation which is familiar to a laboratory user. In the particular result shown in FIG. 12, the samples are labeled as follow:

C—control
D1—glucose
D2—maltose
D3—maltotriose
D5—maltopentaose
D7—maltoheptaose
DL—ladder containing all five sugars Simplifying the optical detection system design of the CarbCE system for carbohydrate analysis was done by utilizing fiber optics and micro-optics fluorescence detection technologies. The design reduces the overall manufacturing cost, while improving the reliability of the instrument. In addition that the chemistry cost per test is less than half that of slab gel systems, the system produces high resolution and detection sensitivity only found in the high-end capillary gel electrophoresis systems (the larger and costly sequencing type instruments).

It has been demonstrated that the gel cartridge with an integrated gel-reservoir under the above mentioned running conditions is able to achieve multiple runs (more than 400 runs) with reproducible results (substantially the same separation efficiency, migration time and resolution) with no need for gel replacement and column cooling devices. Cartridge life tests have shown that after continuous high voltage runs the gel matrix does not degrade since it is drawing low operating currents with constant applied DC voltages. Shorter separation times (<5-10 minutes) prevent high voltage shock, reduced operating temperatures and longer gel-cartridge life. The gel-cartridge system/device is used for multiple electrophoresis runs (250 or more) in an automated electrophoresis device of the CarbCE without gel replacement, which provides advantages for non stop, high-throughput, fast sample screening and very low-cost per sample applications.

The multi-channel CE carbohydrate analysis system in accordance with the present invention improves the speed of separation and resolution of carbohydrate molecules. Benefits of the system over slab gel electrophoresis include time savings (reducing separation time from 3 to 4 hr with slab gel methods to 10 min with the inventive system); labor and consumable reduction (reducing the possibility of human error by eliminating manual intervention, while reducing testing material such as gel, buffer, dye, and markers by 50%); increased sensitivity, resolution and biohazardous waste reduction.

While the invention has been particularly shown and described with reference to the preferred embodiments, it will be understood by those skilled in the art that various changes in form and detail may be made without departing from the spirit, scope, and teaching of the invention.

For example, interface mechanisms may be adapted to receive capillary cartridges of other structural designs. By way of example and not limitation, the detection scheme of the present invention is described in connection with capillary electrophoresis and radiation induced fluorescence detection. It is understood that the present invention is also applicable to detection of radiation emissions other than fluorescence emissions, including other types of emissive radiation, such as phosphorescence, luminescence and chemiluminescence, as well as UV and Visible absorbance based detection. Furthermore, while the separation channels in the described embodiments are defined by cylindrical columns or tubes, it is understood that the concepts of the present invention is equally applicable to separation channels defined by channels, for example micro-channels (such as square, rectangular or essentially semicircular cross sections) defined by etching or micro-machining in a substrate (micro-fluidics type devices or bio-chips).

Accordingly, the disclosed invention is to be considered merely as illustrative and limited in scope only as specified in the appended claims.

We claim:

1. A cartridge for bio-analysis, comprising:
a body;
a plurality of capillaries supported by the body;
a reservoir common to the capillaries; and
a linear gel matrix formulated for electrophoretic analysis of carbohydrate contained in the reservoir, wherein the gel matrix comprises a linear polymer solution as a gel sieving matrix, wherein the linear polymer solution comprises:

| — | mwt g/mol | Concentration |
|---|---|---|
| PEO | 7000000 | 0.000607 mM |
| PEO | 900000 | 0.002777778 mM |
| MOPS | — | 12.5 mM |
| Tris | — | 7.85 mM |
| NP40 | — | 0.05% |
| NaN3 | — | 1 mM |
| EtBr | — | 10 mM. |

2. A bio-analysis system, comprising:
a base;
a cartridge as in claim 1;
a cartridge interface support on the base, interfacing with the cartridge system; and
a controller operatively coupled to the cartridge interface to control operations of the cartridge interface.

3. The cartridge of claim 1, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

4. A method of carbohydrate detection/analysis, comprising:
providing a cartridge, which comprises:
a body;
a plurality of capillaries supported by the body;
a reservoir common to the capillaries; and
a linear gel matrix formulated for electrophoretic analysis of carbohydrate contained in the reservoir;
introducing a carbohydrate sample into one end of each capillary;
undertaking electropherisis separation along each capillary, to separate the carbohydrate sample into components to be analyzed
wherein the gel matrix comprises a linear polymer solution as a gel sieving matrix, wherein the linear polymer solution comprises:

|  | mwt g/mol | Concentration |  |
|---|---|---|---|
| PEO | 7000000 | 0.000607 | mM |
| PEO | 900000 | 0.002777778 | mM |
| MOPS | — | 12.5 | mM |
| Tris | — | 7.85 | mM |
| NP40 | — | 0.05% | |
| NaN3 | — | 1 | mM |
| EtBr | — | 10 | mM. |

5. The method of claim 4, wherein the gel matrix comprises a linear polymer solution as a gel sieving matrix, wherein the linear polymer solution comprises between about 0.01% and about 1.5% polyethylene oxide ("PEO"); between about 0.0% and less than about 2.0% of a second polyethylene oxide ("PEO"); between about 0.0% and about 2.0% of a surfactant; between about 0.0% and about 99% of a polyol; and between about 0.0M and about 1.0M of a pH buffer, where the composition has a pH of between about 2.0 and about 10.0.

6. A cartridge for bio-analysis, comprising:
a body;
a plurality of capillaries supported by the body;
a reservoir common to the capillaries; and
a gel matrix formulated for electrophoretic analysis of carbohydrate contained in the reservoir, wherein the gel matrix comprises a polymer solution as a gel sieving matrix, wherein the polymer solution comprises first and second long polyethylene oxide (PEO) polymers having substantially different molecular weights, each in a very small concentration, wherein the first and second long PEO polymers are about 7.8 times different in molecular weights.

7. The cartridge of claim 6, wherein the first and second long PEO polymers have different concentrations.

8. The cartridge of claim 7, wherein the concentrations of the first and second long PEO polymers are substantially different.

9. The cartridge of claim 6, wherein the concentration of the first long PEO polymer is about 0.000607mM.

10. The cartridge of claim 9, wherein the concentration of the second long PEO polymer is about 0.002777778mM.

11. The cartridge of claim 6, wherein the concentration of the second long PEO polymer is about 0.002777778mM.

12. The cartridge of claim 6, wherein the molecular weight of the first long PEO polymer is about 7000000 mwt g/mol.

13. The cartridge of claim 12, wherein the molecular weight of the second long PEO polymer is about 900000 mwt g/mol.

14. The cartridge of claim 6, wherein the molecular weight of the second long PEO polymer is about 900000 mwt g/mol.

15. The cartridge of claim 6, wherein the molecular weight of the first long PEO polymer is larger than the molecular weight of the second long PEO polymer, and the concentration of the first long PEO polymer is smaller than the concentration of the second long PEO polymer.

16. The cartridge of claim 15, wherein the concentrations of the first and second long PEO polymers are substantially different.

17. The cartridge of claim 16, wherein the first long PEO polymer has a molecular weight of substantially 7000000 mwt g/mol and a concentration of substantially 0.000607mM, and the second long PEO polymer has a molecular weight of substantially 900000 mwt g/mol and a concentration of substantially 0.002777778mM.

18. The cartridge of claim 6, wherein the first and second long PEO polymers are linear polymers.

19. The cartridge of claim 6, wherein the gel matrix comprises a linear polymer solution as a gel sieving matrix, wherein the linear polymer solution comprises between about 0.01% and about 1.5% of the first long PEO polymer; between about 0.0% and less than about 2.0% of the second long PEO polymer; between about 0.0% and about 2.0% of a surfactant;
between about 0.0% and about 99% of a polyol; and between about 0.0M and about 1.0M of a pH buffer, where the composition has a pH of between about 2.0 and about 10.0.

20. A method of carbohydrate detection/analysis, comprising:
providing a cartridge, which comprises:
a body;
a plurality of capillaries supported by the body;
a reservoir common to the capillaries; and
a gel matrix formulated for electrophoretic analysis of carbohydrate contained in the reservoir;
introducing a carbohydrate sample into one end of each capillary;
undertaking electropherisis separation along each capillary, to separate the carbohydrate sample into components to be analyzed, wherein the gel matrix comprises a polymer solution as a gel sieving matrix, wherein the polymer solution comprises first and second long PEO polymers having substantially different molecular weights, each in a very small concentration, wherein the first and second long PEO polymers are about 7.8 times different in molecular weights.

* * * * *